United States Patent [19]

Sato et al.

[11] Patent Number: 4,950,465

[45] Date of Patent: Aug. 21, 1990

[54] PHARMACEUTICAL COMPOSITION FOR RELIEVING SIDE EFFECTS OF PLATINUM-CONTAINING DRUGS

[75] Inventors: Toshio Sato, Tokushima; Yoshinosuke Fukuchi; Kenji Toba, both of Tokyo, Japan

[73] Assignee: Mochida Pharmaceutical Co., Ltd., Tokyo, Japan

[21] Appl. No.: 307,686

[22] Filed: Feb. 7, 1989

[30] Foreign Application Priority Data

Feb. 8, 1988 [JP] Japan ................................ 63-26918

[51] Int. Cl.$^5$ ..................... A61K 35/22; A61K 33/24; A61K 31/28
[52] U.S. Cl. .................................... 424/10; 424/649; 424/545; 514/492
[58] Field of Search .......................................... 424/10

[56] References Cited

FOREIGN PATENT DOCUMENTS 60-28928 2/1985 Japan .
62-106021 5/1987 Japan .
2174905 11/1986 United Kingdom ................. 424/10

OTHER PUBLICATIONS

Chemical Abstracts 106:207421r (1987).
Chemical Abstracts 108:110567w (1988).
Chemical Abstracts, vol. 106, Abstract No. 169266j (1987), pp. 89–90.
Chemical Abstracts, vol. 108, Abstract No. 106109f (1988), p. 33.
Chemical Abstracts, vol. 108, Abstract No. 219525g (1988), p. 375.
Yamamura et al., "Clinical Evaluation of MR-20 for Various Shocks," *Progress in Medicine, vol. 129, pp. 730–738, 1984.*
Honjo et al., "Clinical Effects of MR-20 for Various Pancreatitis," *Progress in Medicine*, vol. 129, pp. 70–83, 1984; and
Proksch et al., "The Purification of the Trypsin Inhibitor From Human Pregnancy Urine," *Journal of Laboratory Clinical Medicine*, vol. 79, pp. 491–499, 1972.

Primary Examiner—Jerome D. Goldberg
Attorney, Agent, or Firm—Burns, Doane, Swecker & Mathis

[57] ABSTRACT

A pharmaceutical composition for relieving side effects of platinum-containing drugs, containing an effective component of ulinastatin is provided. The platinum-containing drugs such as cisplatinum cause serious side effects including kidney dysfunction. The kidney dysfunction, particularly the one caused by a disorder or uriniferous tubule may be significantly relieved by administering the ulinastatin-containing agent of the present invention.

4 Claims, 3 Drawing Sheets

PHARMACEUTICAL COMPOSITION FOR RELIEVING SIDE EFFECTS OF PLATINUM-CONTAINING DRUGS

BACKGROUND OF THE INVENTION

This invention relates to a pharmaceutical composition for relieving side-effects, particularly dysfunction of the kidneys caused by the administration of platinum-containing drugs such as cisplatinumum (cisplatin, cis-diamminedichloroplatinum (II)).

The platinum-containing drugs including cisplatinum are potent carcinostatics employed in many clinical fields, and known to have marked effects on orchioncus, bladder cancer, pyeloureteral tumor, prostatic cancer, ovarian cancer, cancer of the head and neck, lung cancer, and the like.

Cisplatinum, however, has serious side effects including kidney dysfunction. These side effects, which have been known ever since the development of cisplatinum, are dose limiting factors in the administration of cisplatinum which significantly delimits its clinical utility.

The kidney dysfunction caused by the administration of cisplatinum is histopathologically a disorder of proximal uriniferous tubule near its $S_3$ segment, which results in acute turbulorrhexis or necrosis of the uriniferous tubule. The disorder of the proximal uriniferous tubule may clinically be detected by increased values of blood urea nitrogen (BUN), creatinine, fractional excretion of Na (FENa), $\gamma$-glutamyltranspeptitase ($\gamma$-GTP), and N-acetyl-$\beta$-D-glucosaminidase (NAG) in urine.

Accordingly, there has been a strong clinical need for the development of means for relieving the kidney dysfunction caused by cisplatinum.

Japanese Patent Application Kokai No. 60-28928 discloses that fosfomycin can relieve the side effects caused by the administration of carcinostatics including platinum-containing agents such as cisplatinum, anthracycline-based carcinostatics, and nitrosourea-based carcinostatics. In Example 2, fosfomycin significantly suppressed development of the kidney dysfunction caused by cisplatinum as evidenced by reduced increase of BUN and creatinine values in a group wherein a combination of cisplatinum and fosfomycin is administered over a group wherein cisplatinum is solely administered.

Japanese Patent Application Kokai No. 62-106021 discloses administering elastase together with cisplatinum to relieve the side effects including the kidney dysfunction caused by the cisplatinum.

It is also reported that cisplatinum is capable of activating hyaluronidase which participates in the development of kidney dysfunction and various hyaluronidase inhibitors including sodium azulenesulfonate which are effective in relieving kidney dysfunction.

All of the substances used in the above-mentioned prior art documents are foreign and exogenous to the human body. Fosfomycin is a substance produced by a microorganism, is *Streptomyces fragiae*. Elastase is a protein generally derived from porcine pancreas. Hyaluronidase-inhibiting substances are also foreign to the human body. Accordingly, there is a need for developing a less-dangerous endogenous agent for relieving kidney dysfunction caused by cisplatinum.

The inventors of the present invention have made various investigations to find reliable means for avoiding kidney dysfunction, which is clinically the most serious and troublesome side effect caused by the administration of cisplatinum. After such an investigation, the inventors have found that ulinastatin (urinastatin), which is a human urinary trypsin inhibitor, is markedly effective for relieving the side effects, particularly the kidney dysfunction caused by cisplatinum.

SUMMARY OF THE INVENTION

Provided in accordance with the present invention is a pharmaceutical composition for relieving the side effects caused by platinum-containing drugs wherein the effective component of the pharmaceutical composition is ulinastatin.

Also provided is a method for preventing or relieving side effects induced by platinum-containing drugs in a mammal, which comprises administering to said mammal an alleviating or prophylactic amount of an ulinastatin-containing agent.

Further provided is a use of ulinastatin in the manufacture of a pharmaceutical composition for use in preventing or relieving side effects induced by platinum-containing drugs in a mammal, the ulinastatin being in a form suitable for therapeutic administration.

Contemplated by this invention is a pharmaceutical composition as described above wherein said platinum-containing drug is cisplatinum, and wherein said side effect is a dysfunction of the kidney caused by a disorder of the proximal uriniferous tubule.

BRIEF DESCRIPTION OF THE DRAWINGS

FIG. 1 demonstrates changes in the amount of $\gamma$-GTP excreted in urine;

FIG. 2 demonstrates changes in the amount of NAG excreted in urine; and

FIG. 3 demonstrates changes in FENa.

DETAILED DESCRIPTION OF THE INVENTION

Figure 1:
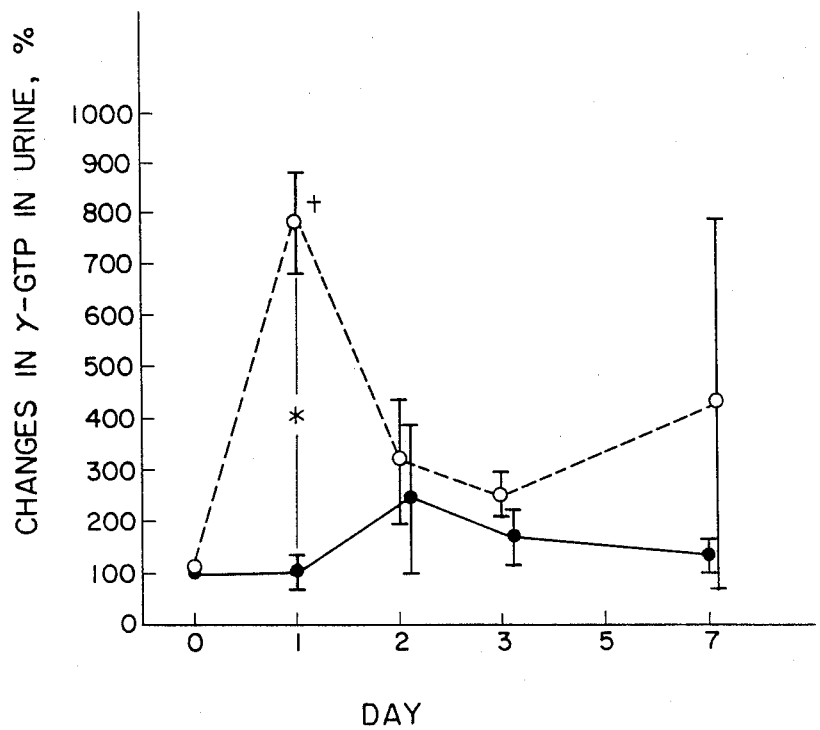
FIGS. 1 to 3 are diagrams illustrating the results of Experiment 2 of the present invention.

Ulinastatin is an acidic glycoprotein generally derived from human urine, and has a molecular weight of about 67,000.

Ulinastatin is a safe substance of human origin. The clinical test and the side effect-investigation report after selling at the market reveal that side effects are developed in as few as 32 cases of 3200 cases (side effect-developing frequency of 1.0%), and the side effects thus developed were far from serious. Moreover, ulinastatin does not express any side effects when it is used in combination with cisplatinum.

Ulinastatin inhibits various enzymes such as trypsin, $\alpha$-chymotrypsin, hyaluronidase, granular elastase, plasmin, etc. and stabilizes lyposomal membranes. Based on these actions, ulinastatin has been clinically employed for treating acute circulation insufficiency caused by hemorrhagic shock, bacterial shock, traumatic shock and burn shock as disclosed in H. Yamamura et al., Igaku-no Ayumi (Progress in Medicine), vol. 129, pages 730–738, 1984, and acute pancreatitis as disclosed in I. Honjo et al., Igaku-no-Ayumi (Progress in Medicine), vol. 129, pages 70–83, 1984.

Ulinastatin is also known to prevent or relieve prerenal acute renal failure (ARF) caused by systemic circulation insufficiency or acute circulation insufficiency which occurs after a surgical operation, and the like. The mechanisms for the action of ulinastatin in these cases are reported to be due to an improvement in systemic circulation insufficiency. More illustratively, it is reported that ulinastatin improves systemic circulation insufficiency, and as a result of such an improvement in systemic circulation insufficiency, renal failure is secondarily prevented or relieved.

On the other hand, cisplatinum is believed to directly destroy the cells of the uriniferous tubule causing renal ARF. Such a mechanism for the development of renal ARF is clearly different from the mechanism as described above for the prerenal ARF.

The inventors of the present invention have found that ulinastatin relieves kidney dysfunction through a direct protection of the uriniferous tubule and not through the indirect improvement of systemic circulation insufficiency as described above for the prerenal ARF. Based on this finding, the present inventors have found that ulinastatin may be used for relieving kidney dysfunction caused by administration of cisplatinum. Therefore, the use of ulinastatin for relieving the cisplatinum-induced kidney dysfunction according to the present invention is quite unique and never expected from the prior art.

Ulinastatin may be prepared as described below in accordance with, for example, the process disclosed in Proksch et al., "The purification of the trypsin inhibitor from human pregnancy urine", J. Lab. Clin. Med., vol. 79, pages 491-499, 1972.

Preparation of ulinastatin

A 650 liter portion of pooled urine taken from normal human adults was concentrated and dialyzed against demineralized water. The pH of the urine was adjusted to pH 7.8 through a DEAE cellulose column of 20×80 cm equilibrated with 0.05M Tris-HCl buffer solution, pH 7.8 to adsorb ulinastatin onto the column. The column was then washed with 40 liters of the Tris-HCl buffer solution. The ulinastatin adsorbed onto the column was then eluted with a Tris-HCl buffer solution containing 0.3M sodium chloride. The effluent was heated at 60° C. for 20 minutes to an inactivate proteases contained therein to produce 16 grams of crude ulinastatin. The crude urinastatin was absorbed onto a DEAE cellulose column of 8×60 cm equilibrated with 0.02M glycine-HCl buffer solution, pH 3.4. The column was then washed with 10 liters of the glycine-HCl buffer solution, and further washed with 10 liters of the glycine-HCl buffer solution containing 0.2M sodium chloride. Ulinastatin was then eluted from the column with 8 liters of the glycine-HCl buffer solution containing 0.4M sodium chloride. The effluent was concentrated by ultraconcentration. The ultraconcentrate was subjected to a gel chromatography on a column of 10×95 cm filled with Sephadex G-100 by employing physiologic saline as the developing media to obtain purified ulinastatin. The thus obtained, purified ulinastatin was an acidic glycoprotein having a molecular weight of 67,000, isoelectric point of pH 2 to 3, carbohydrate content of 5 to 12%, and specific activity of about 2500 units/mg. The activity of ulinastatin is calculated such that 1 unit of ulinastatin inhibits 50% of the activity of 2 micrograms of trypsin.

The effects of ulinastatin for improving the kidney dysfunction caused by cisplatinum are hereinafter demonstrated by the following Experiments.

Experiment 1: Animal Experiment (Procedure)

The animals used were ddY male mice having body weight in the range of from 20 to 30 grams.

The BUN value which is indicative of kidney dysfunction was measured for the following three groups.

Group A: a group wherein cisplatinrm was solely administered.

To the mice, 16 mg/kg of cisplatinum was subcutaneously administered once, and physiologic saline was continuously administered intravenously from the day when cisplatinum was administered. Cisplatinum was dissolved in saline to a concentration of 1.6 mg/ml, and an amount of 0.1 ml per body weight of 10 grams was administered.

Group B: a group wherein cisplatinum was administered together with ulinastatin.

To the mice, 16 mg/kg of cisplatinum was subcutaneously administered once, and 100,000 units/kg of ulinastatin was continuously administered intravenously once a day from the day of cisplatinum administration for 2, 3 and 5 days, respectively. Cisplatinum was dissolved in saline to a concentration of 1.6 mg/ml, and an amount of 0.1 ml per body weight of 10 g was administered. Ulinastatin was dissolved in saline to a concentration of 10,000 units/ml, and an amount of 0.1 ml per body weight of 10 grams was administered.

Group C: a group wherein no treatment was made.

No treatment was carried out.

(Results)

The results are shown in Table 1.

TABLE 1

| | BUN (mg/dl) after administration of cisplatinum | | |
|---|---|---|---|
| | Time after cisplatinum administration (day) | | |
| | 2 | 3 | 5 |
| Group A (cisplatinum) | 26.8 ± 1.8** (10*) | 56.2 ± 11.1** (10*) | 177.4 ± 7.9** (11*) |
| Group B (cisplatinum + ulinastatin) | 19.9 ± 1.1** (7*) | 39.1 ± 4.5** (17*) | 71.1 ± 12.4**++ (11*) |
| Group C (No treatment) | 19.7 ± 1.2 (7*) | 17.6 ± 0.9 (10*) | 25.6 ± 1.2 (10*) |

Results are given as mean ± standard error.
*Number of mice
**Significantly different from group C at $p < 0.01$
++Significantly different from group A at $p < 0.01$.

As shown in Table 1, in group A, the administration of cisplatinum induced an increase in BUN value clearly indicating kidney dysfunction. In group B, an increase in BUN value induced by cisplatinum was clearly suppressed.

As evident from the above results, ulinastatin clearly relieved the kidney dysfunction induced by cisplatinum.

Experiment 2: Clinical test (Procedure)

Ulinastatin was administered to patients with bronchogenic carcioma, and γ-GTP and NAG excreted into urine, as well as FENa were measured and compared.

The patients with bronchogenic carcinoma were divided into two groups. 7 patients were administered cisplatinum, whereas 8 patients (7 patients in the measurement of γ-GTP) were administered cisplatinum and ulinastatin.

γ-GTP activity was measured by the L-γ-glutamyl-p-nitroanilide substrate method.

NAG was measured in an automatic analyzer (model 726, manufactured by Hitachi, Ltd.) by using the NAG Test-Shionogi.

FENa was calculated from values of Na and creatinine in plasma and urine.

In the group wherein cisplatinum was administered, 50 mg/m² of body surface area of cisplatinum was dissolved in 500 ml of physiologic saline, and the thus prepared solution was intravenously infused into the patient for 2 hours. Cisplatinum was administered once. Intravenously infused into the patient was 1000 ml of 5% glucose solution before administering cisplatinum, 1000 ml of physiologic saline after administration of cisplatinum, and 200 ml of electrolyte solution on the next day for the purpose of diuresis.

In the group wherein cisplatinum was administered together with ulinastatin, cisplatinum was administered in the same manner as the above-described group, and ulinastatin was intravenously infused into the patient for two days on the very day (the first day) and the next day (the second day) of cisplatinum administration by dissolving ulinastatin into the solutions as described above. On the first day, 100,000 units of ulinastatin were administered before the administration of cisplatinum, and 500,000 units of ulinastatin were administered after the administration of cisplatinum, and on the second day, 300,000 units of ulinastatin were administered.

(Results)

Figure 2:
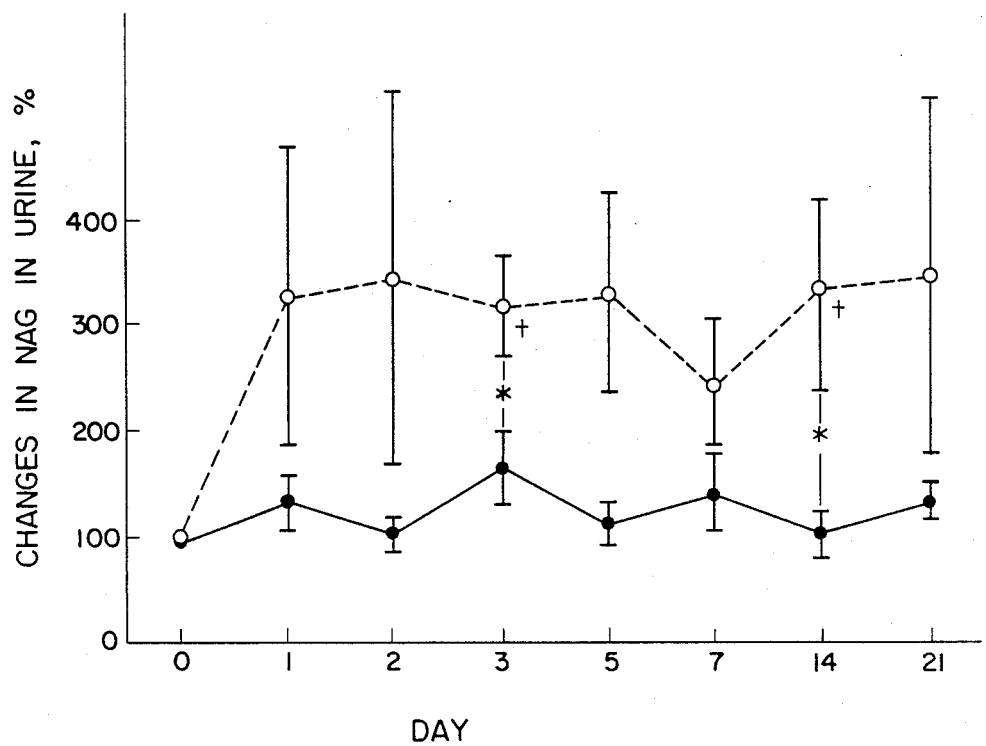
Figure 3:
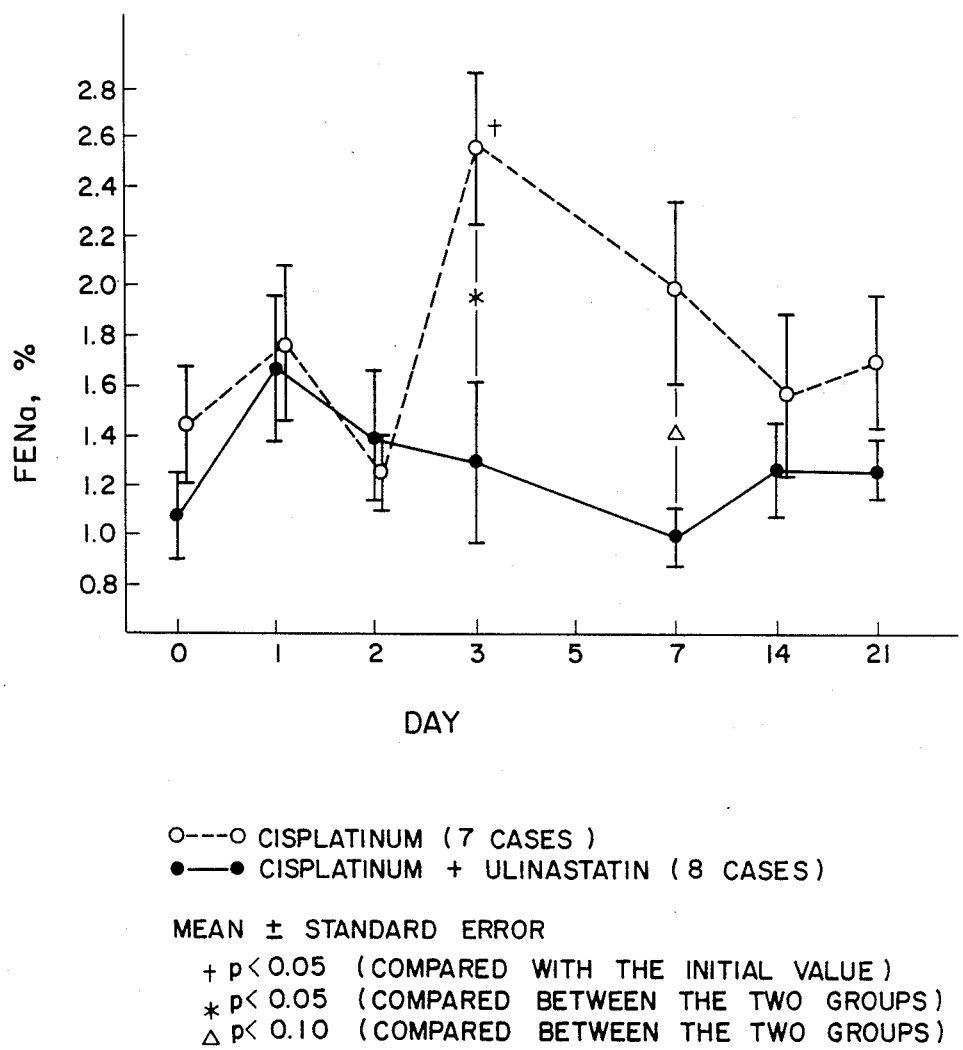

The results are shown in FIGS. 1 to 3.

FIG. 1 demonstrates changes in the amount of γ-GTP excreted in urine, and FIG. 2 demonstrates changes in the amount of NAG excreted in urine. The changes in FIGS. 1 and 2 are demonstrated as percent changes based on the values before the cisplatinum administration of 100%.

FIG. 3 demonstrates changes in FENa in actual measurements.

After administering cisplatinum, increase in the values of γ-GTP in urine, NAG in urine and FENa were all recognized, clearly indicating nephrotoxicity induced by cisplatinum. Ulinastatin evidently suppressed the thus increased values of γ-GTP in urine, NAG in urine and FENa.

γ-GTP is an enzyme which is abundant in the membranes of uriniferous tubule cells. NAG is one of the lysosomal enzymes in the uriniferous tubule. FENa is an indicator of Na reabsorption through the uriniferous tubule, which is widely used for making differential diagnosis of acute renal failure. The measurements carried out in this Experiment, therefore, are well indicative of nephrotoxicity induced by cisplatinum, particularly the disorder of the uriniferous tubule where toxicity of cisplatinum is developed.

As demonstrated in the above-described results, ulinastatin clearly relieved nephrotoxicity induced by cisplatinum.

Experiment 3: Acute toxicity

To a group of 10 ddY male mice having body weight of 20 to 22 grams 4g/kg of ulinastatin was intravenously or intraperitoneally administered. Symptom and change in the weight were observed for a period of 1 week. The weight change was identical with that of the control group, and no mice died during the experimental period.

Conventional administration of cisplatinum has generally been carried out by dissolving a predetermined amount of cisplatinum in physiologic saline or glucose-NaCl solution, intravenously infusing the cisplatinum-containing solution once a day for 1 day to several days, ceasing the administration for 1 to 3 weeks, and repeating the abovedescribed procedure several times.

Ulinastatin may preferably be administered everyday for 2 to 28 days from the day of cisplatinum administration. Ulinastatin may be administered at 5 to 5,000,000 units, preferably from 200,000 to 600,000 units per day, although its dose may be increased or decreased in accordance with the symptoms of the patient or the manner of administration.

Ulinastatin may be administered before, after or simultaneously with cisplatinum by dissolving in an adequate solution.

The side effect-relieving agent for platinum-containing drugs according to the present invention contains ulinastatin as the effective component, and may preferably be administered intravenously as a parenteral preparation such as by injection or infusion. The parenteral preparation may preferably be lyophilized so that it can be dissolved at the time of administration. The ulinastatin-containing agent may be prepared in accordance with the conventional processes, and may contain various vehicles, adjuvants, and additives as desired.

Example 1: Preparation of lyophilized injection

To 2000 ml of physiologic saline, 40 grams of ulinastatin was dissolved, and the solution was aseptically filtered by means of a membrane filter. A 1 ml portion of the filtrate was filled into a sterilized glass container and lyophilized in accordance with the conventional method to produce a lyophilized preparation.

What is claimed is:

1. A method for preventing or relieving side effects induced by the administration of cisplatinum to a mammalian organism, said method comprising administering by injection of intravenous infusion to a mammalian organism in need of such prevention or relief an effective cisplatinum-side effect relieving amount of ulinastatin.

2. The method according to claim 1, wherein said ulinastatin is administered at 5 to 5,000,000 units per day.

3. The method according to claim 2, wherein said ulinastatin is administered at 200,000 to 600,000 units per day.

4. The method according to claim 1, wherein said cisplatinum-side effect is kidney dysfunction.

* * * * *